United States Patent
Sauer

(10) Patent No.: US 10,092,317 B2
(45) Date of Patent: Oct. 9, 2018

(54) THORACIC CANNULA, OBTURATOR, AND ASSEMBLY THEREOF

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 0 days.

(21) Appl. No.: 15/410,916

(22) Filed: Jan. 20, 2017

(65) Prior Publication Data

US 2017/0209172 A1 Jul. 27, 2017

Related U.S. Application Data

(60) Provisional application No. 62/286,068, filed on Jan. 22, 2016.

(51) Int. Cl.

| A61B 17/34 | (2006.01) |
| A61M 25/06 | (2006.01) |
| A61M 25/01 | (2006.01) |
| A61M 25/02 | (2006.01) |
| A61M 25/00 | (2006.01) |
| A61B 17/00 | (2006.01) |

(52) U.S. Cl.
CPC ..... *A61B 17/3421* (2013.01); *A61M 25/0043* (2013.01); *A61M 25/0102* (2013.01); *A61M 25/02* (2013.01); *A61M 25/0662* (2013.01); *A61B 2017/00477* (2013.01); *A61B 2017/349* (2013.01); *A61B 2017/3427* (2013.01); *A61B 2017/3454* (2013.01); *A61B 2017/3484* (2013.01); *A61B 2017/3492* (2013.01); *A61M 2025/006* (2013.01); *A61M 2025/0286* (2013.01)

(58) Field of Classification Search
CPC ...... A61B 17/3421; A61B 2017/00477; A61B 2017/3427; A61B 2017/3454; A61B 2017/3484; A61B 2017/349; A61B 2017/3492; A61M 25/0043; A61M 25/0102; A61M 25/02; A61M 25/0662; A61M 2025/006; A61M 2025/0286
USPC ........................ 604/170.02, 170.01
See application file for complete search history.

(56) References Cited

U.S. PATENT DOCUMENTS

| 6,394,979 | B1 * | 5/2002 | Sharp | A61M 5/32 604/117 |
| 6,471,700 | B1 * | 10/2002 | Burbank | A61B 10/0266 600/562 |
| 7,693,567 | B2 | 4/2010 | Tsonton | |
| 8,152,828 | B2 | 4/2012 | Taylor | |

FOREIGN PATENT DOCUMENTS

| EP | 2432408 | 3/2016 |
| WO | WO2007048083 | 4/2007 |

\* cited by examiner

*Primary Examiner* — Manuel Mendez
(74) *Attorney, Agent, or Firm* — Christopher B. Miller

(57) ABSTRACT

A surgical assembly is disclosed. The assembly has a cannula. The cannula has an oblong opening on a proximal end, one or more textured features on an outside, and a stabilizer at the proximal end. The assembly also has an obturator sized to fit within the cannula from the proximal end of the cannula. The obturator has a tapered end configured to extend from the distal end of the cannula and a protrusion on a proximal end of the obturator configured to engage a portion of the cannula.

6 Claims, 5 Drawing Sheets

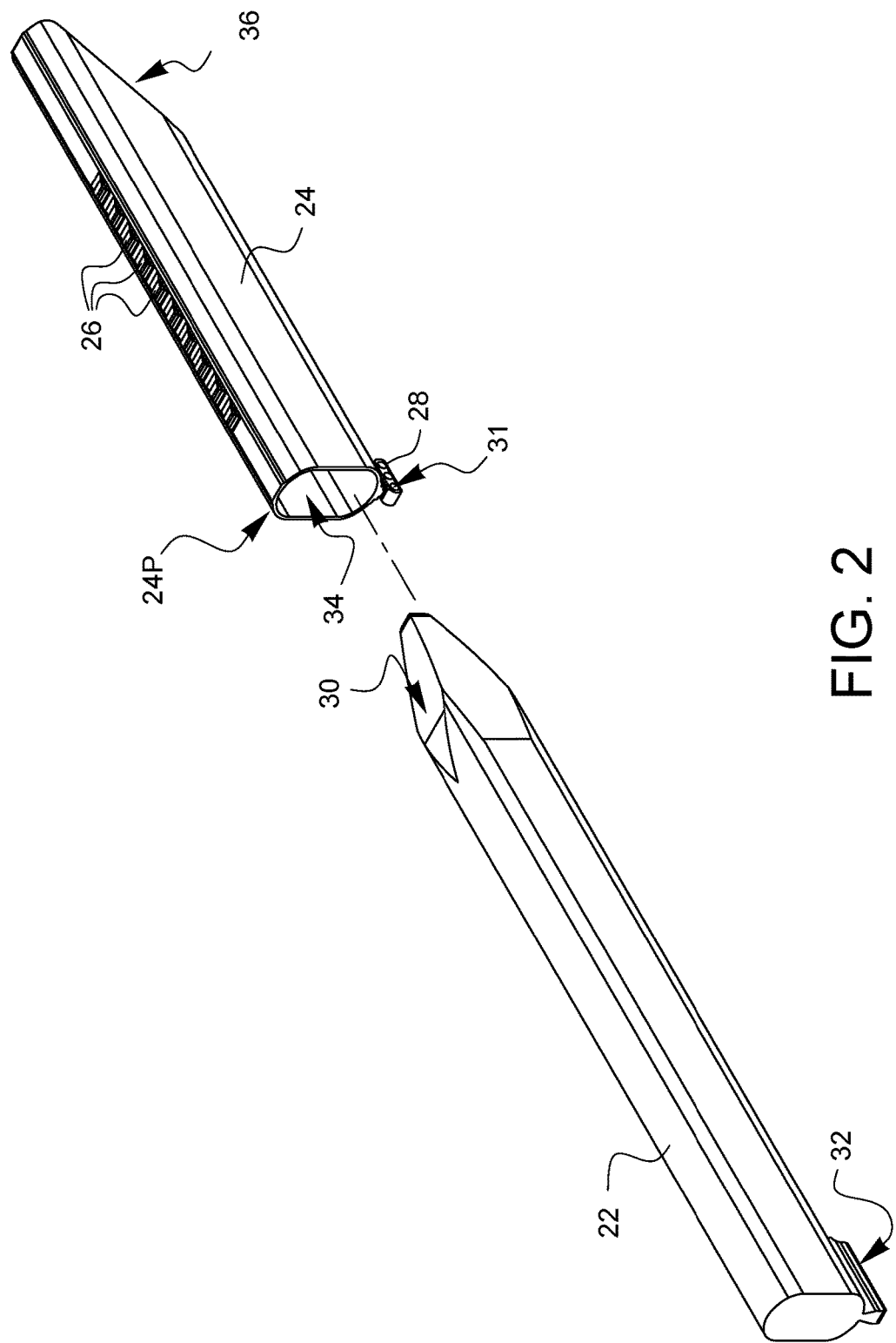

THORACIC CANNULA, OBTURATOR, AND ASSEMBLY THEREOF

RELATED APPLICATION

This patent application claims priority to U.S. Provisional Patent Application No. 62/286,068 filed Jan. 22, 2016 and entitled "THORACIC CANNULA, OBTURATOR, AND ASSEMBLY THEREOF". The 62/286,068 application is hereby incorporated by reference in its entirety.

FIELD

The claimed invention relates to surgical devices, and more specifically to cannulas and obturators.

BACKGROUND

Laparoscopic, endoscopic, and other types of minimally invasive surgical procedures often rely on percutaneous introduction of surgical instruments into an internal region of a patient where the surgical procedure is to be performed. It would be desirable to have an improved cannula and obturator device for providing percutaneous access.

SUMMARY

A surgical assembly is disclosed. The assembly has a cannula. The cannula has an oblong opening on a proximal end, one or more textured features on an outside, and a stabilizer at the proximal end. The assembly also has an obturator sized to fit within the cannula from the proximal end of the cannula. The obturator has a tapered end configured to extend from the distal end of the cannula and a protrusion on a proximal end of the obturator configured to engage a portion of the cannula.

Another surgical assembly, is disclosed. The assembly has a cannula. The cannula has an oblong opening on a proximal end and an angled opening on a distal end. The cannula also has one or more textured features on an outside and a stabilizer at the proximal end. The stabilizer defines one or more holes configured to receive suture. The assembly also has an obturator sized to fit within the cannula from the proximal end of the cannula. The obturator has a tapered end configured to extend from the distal end of the cannula and a protrusion on a proximal end of the obturator configured to engage the stabilizer so that the protrusion does not press on the cannula opening. The cannula further has a pair of short sides and a pair of long sides. The one or more textured features on the outside of the cannula are located on at least one of the short sides of the cannula.

BRIEF DESCRIPTION OF THE DRAWINGS

FIG. 2 is an exploded perspective view of the obturator-cannula assembly from FIG. 1B.

Figure 1A:
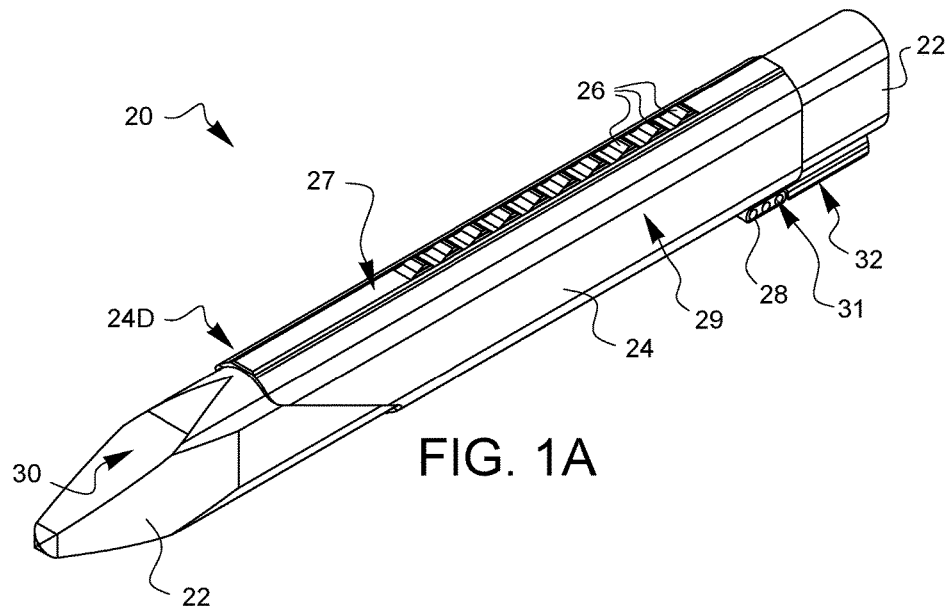
FIG. 1A is a perspective view of an assembly, from a distal perspective, which includes an obturator and a cannula.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

Figure 1B:
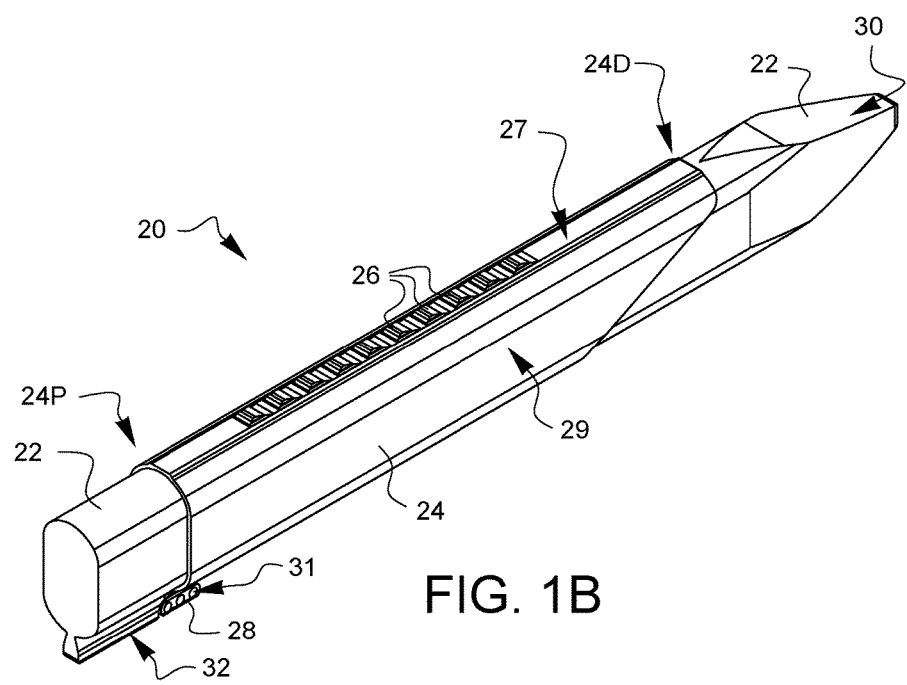
FIG. 1B is a perspective view of the assembly of FIG. 1A, from a proximal perspective.
Figure 3D:
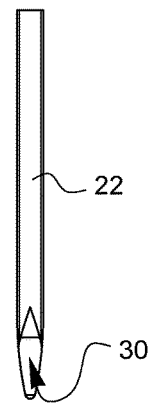
FIGS. 3A, 3B, 3C, 3D, 3E, and 3F are distal, left, right, top, bottom, and proximal elevational views, respectively, of the obturator of FIGS. 1A, 1B, and 2.
Figure 3B:
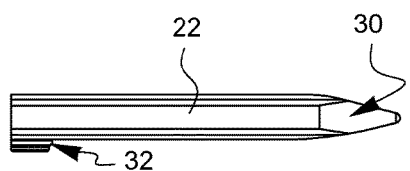
Figures 3A, 3C:
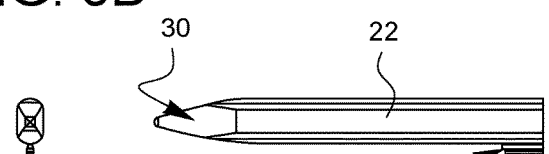
Figure 3E:
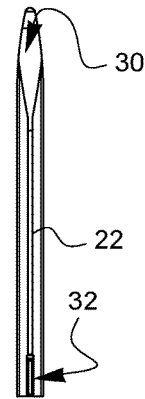
Figure 3F:

FIG. 1A is a perspective view of an assembly 20, from a distal perspective, which includes an obturator 22 and a cannula 24. FIG. 1B is a perspective view of the assembly 20, from a proximal perspective. The assembly 20 is intended to be inserted in an intercostal space in an incision made between a patient's ribs to provide thoracic access. The cannula 24 has one or more textured features 26 on one or more sides of the cannula 24. The textured features 26 allow easy insertion of the cannula 24 into an incision as well as reasonably easy repositioning while precluding inadvertent slip out of the cannula 24 from the incision site.

Figure 4D:
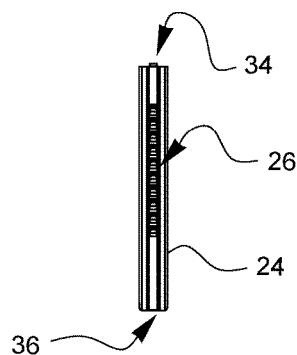
FIGS. 4A, 4B, 4C, 4D, 4E, and 4F are distal, left, right, top, bottom, and proximal elevational views, respectively, of the cannula of FIGS. 1A, 1B, and 2.
Figure 4B:
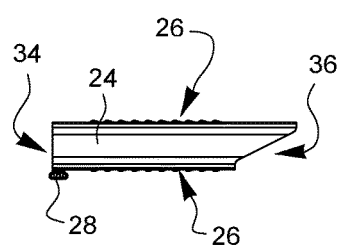
Figure 4A:
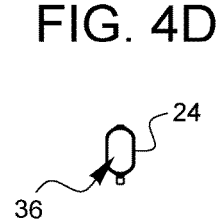
Figure 4C:
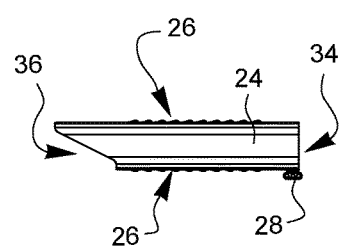
Figure 4E:
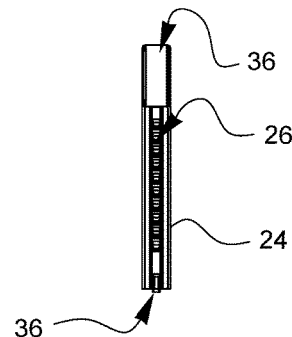
Figure 4F:
Figure 5D:
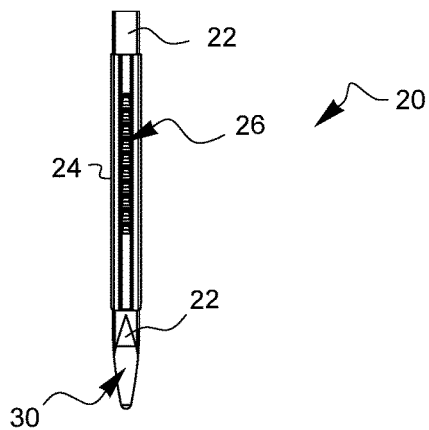
FIGS. 5A, 5B, 5C, 5D, 5E, and 5F are distal, left, right, top, bottom, and proximal elevational views, respectively, of the obturator-cannula assembly of FIG. 1.
Figure 5B:
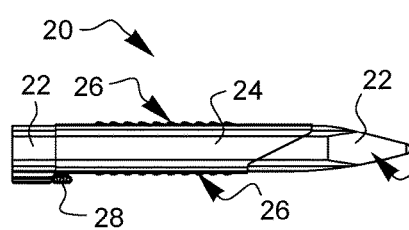
Figure 5A:
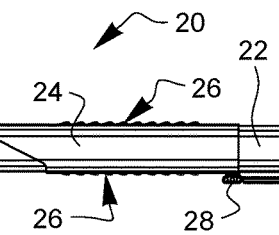
Figure 5C:
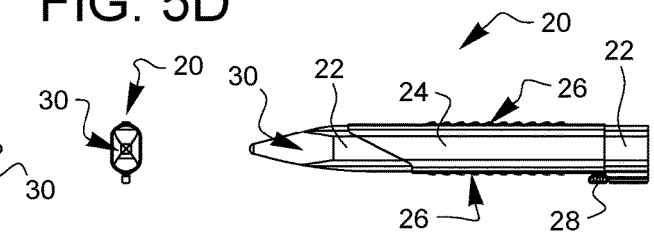
Figure 5E:
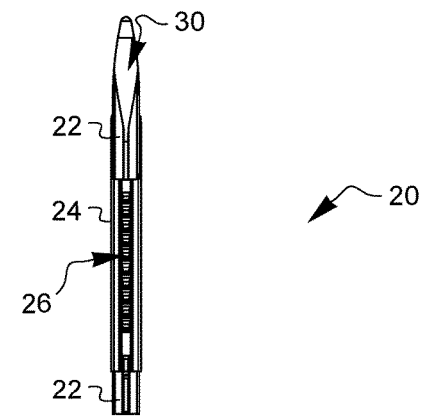
Figure 5F:

The cannula 24 has a rounded rectangular cross-sectional shape which may be seen in FIG. 4A. This rounded rectangular cross-sectional shape has two pairs of opposite sides separated by rounded corners. One pair of opposite sides is longer than the other. Referring back to FIG. 1A, the textured features 26 are preferably located along the sides of the cannula corresponding to the shorter sides in the rounded rectangular cross-sectional shape. These shorter sides 27 are oriented such that they will not face the ribs through which the cannula 24 may be placed. Therefore, the textured features 26 will not be facing the blood vessels and nerves which follow the edges of the ribs and therefore will tend not to contact such fragile structures. Instead, the textured features 26 can grab into the less sensitive muscle tissue between the ribs. By contrast, the longer sides 29 of the cannula 24, which are preferably smooth, will face and may come into contact with the blood vessels and nerves which follow the edges of the ribs. These smooth surfaces may help to minimize the opportunity for damage to such nerves and/or blood vessels.

The cannula 24 also has a stabilizer 28 which defines one or more suturing holes 31 which are configured to receive suture that can be anchored to surrounding tissue or other objects to help stabilize the cannula 24. In this embodiment, the stabilizer 28 is located on the proximal end 24P of the cannula 24, and in particular for this embodiment, the stabilizer 28 is also located on one of the shorter sides 27 at the proximal end 24P.

The distal end of the cannula 24D is angled to allow for a larger opening at the distal end 24D than at the proximal end 24P of the cannula. This larger opening can be used to provide a wider field of view for any endoscope which might be inserted into the cannula, it can also help to provide a wider range of motion for surgical devices placed into the cannula 24.

The obturator 22 has a chiseled or tapered or otherwise angled or wedge-like or pointed end 30 which facilitates introduction of the cannula-obturator assembly 20 into an incision. The distal end 30 of the obturator, however, is preferably not sharp so that damage to tissue is minimized or otherwise avoided. The obturator 22 also has a protrusion 32 on the proximal end of the obturator 22 which is configured to engage the cannula 24 such that when a force is applied to the obturator 22 from the proximal end, the obturator 22 will push the cannula 24 into the incision. The protrusion 32 also prevents the obturator 22 from falling through the cannula 24 and into the patient. The protrusion 32 may also be shaped to engage the stabilizer 28 of the cannula 24 so that the edges of the proximal end 24P of the cannula 24 do not have an opportunity to be bent by contact with the protrusion 32.

FIG. 2 is an exploded perspective view of the obturator-cannula assembly 20 from FIG. 1B. As can be seen in this view, the cannula 24 in this embodiment has a rounded rectangular or oblong opening 34 on its proximal end 24P. Such an opening can help accommodate minimally invasive surgical instruments which have a bend in them while still fitting between a patient's ribs. Furthermore, as discussed previously, the cannula 24 has an angled opening 36 on its distal end to enable a wider field of motion for surgical instruments placed through the cannula 24.

FIGS. 3A, 3B, 3C, 3D, 3E, and 3F are distal, left, right, top, bottom, and proximal elevational views, respectively, of the obturator 22 of FIGS. 1A, 1B, and 2.

FIGS. 4A, 4B, 4C, 4D, 4E, and 4F are distal, left, right, top, bottom, and proximal elevational views, respectively of the cannula 24 of FIGS. 1A, 1B, and 2.

FIGS. 5A, 5B, 5C, 5D, 5E, and 5F are distal, left, right, top, bottom, and proximal elevational views, respectively of the obturator-cannula assembly 20 of FIG. 1.

Various advantages of a thoracic cannula, obturator, and assembly thereof have been discussed above. Embodiments discussed herein have been described by way of example in this specification. It will be apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. The drawings included herein are not necessarily drawn to scale. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. An assembly, comprising:
   a cannula having:
      an oblong opening on a proximal end;
      one or more textured features on an outside; and
      a stabilizer at the proximal end; and
   an obturator sized to fit within the cannula from the proximal end of the cannula, the obturator having:
      a tapered end configured to extend from the distal end of the cannula; and
      a protrusion on a proximal end of the obturator configured to engage a portion of the cannula.

2. The assembly of claim 1, wherein the cannula further comprises an angled opening on a distal end of the cannula.

3. The assembly of claim 1, wherein the protrusion is configured to engage the stabilizer so that the protrusion does not press on the cannula opening.

4. The assembly of claim 1, wherein the stabilizer defines one or more holes configured to receive suture.

5. The assembly of claim 1, wherein the cannula has a pair of short sides and a pair of long sides, and wherein the one or more textured features on the outside of the cannula are located on at least one of the short sides of the cannula.

6. An assembly, comprising:
   a cannula having:
      an oblong opening on a proximal end;
      an angled opening on a distal end;
      one or more textured features on an outside; and
      a stabilizer at the proximal end, the stabilizer defining one or more holes configured to receive suture;
   an obturator sized to fit within the cannula from the proximal end of the cannula, the obturator having:
      a tapered end configured to extend from the distal end of the cannula; and
      a protrusion on a proximal end of the obturator configured to engage the stabilizer so that the protrusion does not press on the cannula opening; and
   wherein the cannula has a pair of short sides and a pair of long sides, and wherein the one or more textured features on the outside of the cannula are located on at least one of the short sides of the cannula.

* * * * *